(12) United States Patent
Guo et al.

(10) Patent No.: US 11,779,398 B2
(45) Date of Patent: Oct. 10, 2023

(54) ROBOTIC STEREOTACTIC SYSTEM FOR MRI-GUIDED NEUROSURGERY

(71) Applicant: THE UNIVERSITY OF HONG KONG, Hong Kong (CN)

(72) Inventors: Ziyan Guo, Hong Kong (CN); Ka Wai Kwok, Hong Kong (CN); Ziyang Dong, Hong Kong (CN); Kit Hang Brian Lee, Hong Kong (CN); Hing Choi Fu, Hong Kong (CN); Chim Lee Cheung, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 606 days.

(21) Appl. No.: 16/955,364

(22) PCT Filed: Jan. 24, 2019

(86) PCT No.: PCT/CN2019/072961
§ 371 (c)(1),
(2) Date: Jun. 18, 2020

(87) PCT Pub. No.: WO2019/144904
PCT Pub. Date: Aug. 1, 2019

(65) Prior Publication Data
US 2021/0015558 A1    Jan. 21, 2021

Related U.S. Application Data

(60) Provisional application No. 62/623,280, filed on Jan. 29, 2018.

(51) Int. Cl.
*A61B 34/20* (2016.01)
*A61B 90/11* (2016.01)
(Continued)

(52) U.S. Cl.
CPC ............. *A61B 34/20* (2016.02); *A61B 34/37* (2016.02); *A61B 90/11* (2016.02); *G01R 33/287* (2013.01);
(Continued)

(58) Field of Classification Search
CPC ......... A61B 34/20; A61B 34/30; A61B 34/37; A61B 34/70; A61B 34/71;
(Continued)

(56) References Cited

U.S. PATENT DOCUMENTS

2006/0155262 A1* 7/2006 Kishi ..................... A61B 34/74
606/1
2008/0097195 A1    4/2008 Urquhart et al.
(Continued)

FOREIGN PATENT DOCUMENTS

CN    102113905 A    7/2011
CN    103417303 A    12/2013
(Continued)

OTHER PUBLICATIONS

Jiang et al.; Design and analysis of a tendon-based MRI-compatible surgery robot for transperineal prostate needle placement; published online on May 7, 2014; Proceedings of the Institution of Mechanical Engineers, Part C: Journal of Mechanical Engineering Science. 2015;229(2):335-348. (Year: 2014).*
(Continued)

*Primary Examiner* — Chao Sheng
(74) *Attorney, Agent, or Firm* — Saliwanchik, Lloyd & Eisenschenk

(57) ABSTRACT

A neurosurgical robotic system for bilateral stereotaxy that integrates intraoperative MRI guidance is provided. The robotic system can be implemented in regular diagnostic MRI facilities. Navigation for bilateral brain targets can be performed independently and simultaneously. The robotic
(Continued)

system includes a plurality of manipulators, a needle guide (31), a needle (12) disposed within the needle guide (31); and a mounting base (39) with a plurality of screw holes for bone mounting.

19 Claims, 12 Drawing Sheets

(51) Int. Cl.
  *G01R 33/28* (2006.01)
  *A61B 90/10* (2016.01)
  *A61B 90/00* (2016.01)
  *A61B 34/37* (2016.01)

(52) U.S. Cl.
  CPC . *A61B 2034/2051* (2016.02); *A61B 2090/103* (2016.02); *A61B 2090/374* (2016.02)

(58) Field of Classification Search
  CPC ...... A61B 2034/715; A61B 2034/2051; A61B 90/11; A61B 2090/374; G01R 33/287
  See application file for complete search history.

(56) References Cited

U.S. PATENT DOCUMENTS

| | | | |
|---|---|---|---|
| 2010/0234856 A1* | 9/2010 | Stoianovici | A61B 90/11 606/130 |
| 2013/0304084 A1* | 11/2013 | Beira | F16H 19/08 74/89.22 |

FOREIGN PATENT DOCUMENTS

| | | |
|---|---|---|
| CN | 105193478 A | 12/2015 |
| CN | 106999248 A | 8/2017 |
| CN | 107049443 A | 8/2017 |

OTHER PUBLICATIONS

Jiang et al.; Modeling and control of a high-precision tendon-based magnetic resonance imaging-compatible surgical robot; published online on May 6, 2015; Proceedings of the Institution of Mechanical Engineers, Part I: Journal of Systems and Control Engineering. 2015;229(8):711-727. (Year: 2015).*

International Search Report and Written Opinion dated Apr. 25, 2019 in International Application No. PCT/CN2019/072961.

* cited by examiner

ROBOTIC STEREOTACTIC SYSTEM FOR MRI-GUIDED NEUROSURGERY

CROSS-REFERENCE TO RELATED APPLICATIONS

This application is the U.S. national stage application of International Patent Application No. PCT/CN2019/072961, filed Jan. 24, 2019, which claims the benefit of U.S. Provisional Application No. 62/623,280, filed Jan. 29, 2018, the disclosure of each of which is incorporated herein by reference in its entirety.

FIELD OF INVENTION

Embodiments of the subject invention relate to medical robots, and particularly to surgical robots for magnetic resonance imaging (MRI)-guided interventions.

BACKGROUND

Stereotaxy is a technique that can locate targets of surgical interest using an external coordinate system as a reference. Its application in functional neurosurgery mostly aims to treat a variety of movement disorders (e.g. Parkinson's disease (PD) and dystonia), psychiatric abnormalities and epilepsy. PD alone is the second most common disease of the nervous system after Alzheimer's disease, and is projected to affect over 8.7 million people worldwide by 2030. Deep brain stimulation (DBS) is one of the common stereotactic procedures, which is a surgical treatment for debilitating motor symptoms of PD and dystonia. Two long (e.g. 300 mm) slender (≈Ø1.3 mm) DBS needles can be individually guided by a stereotactic frame and inserted through Burr holes into the patient's skull. Stimulation electrodes embedded at the tip of needle will then be implanted to the deep brain areas of interest, thus delivering programmed electrical impulses.

Although the standard workflow of stereotactic neurosurgery has been established for over half a century, the operation still remains challenging due to its complicated workflow and its high demand for surgical accuracy. The average recorded error of 2-3 mm is just barely tolerable. Stereotactic navigation could be further complicated by substantial deformation of intracranial contents, namely "brain shift", which occurs inevitably after craniotomy. The shift is mainly caused by gravity, cerebrospinal fluid (CSF) leakage, anesthesia and surgical manipulation. It could induce misalignment (as large as 10-30 mm) of the pre-operative (pre-op) planning path, aiming beyond the actual target. Unlike fluoroscopy/CT, MRI can directly visualize the critical brain structures and targets of interest (e.g. subthalamic nucleus (STN), globus pallidus interna (GPi) or ventral intermediate nucleus).

Currently, there are very limited choices of magnetic resonance (MR) safe stereotactic systems (e.g. NexFrame®, Medtronics Inc., Ireland and ClearPoint®, MRI Interventions Inc., USA). They generally require intensive manual adjustment of the stereotactic frame, and the patient to be transferred in-and-out of the scanner bore.

Compactness and MRI compatibility are two crucial issues regarding the feasibility and adaptability of robots in the regular hospital setup. Very few robotic platforms can fit within the MRI head coil, and also operate during continuous imaging without degrading the image quality. In general, there is no robotic system for functional neurosurgery incorporated with MR safe actuation and MR-based tracking, capable of performing stereotactic manipulation inside the MRI bore.

BRIEF SUMMARY

Embodiments of the subject invention provide an intra-operative MRI-guided robot for bilateral stereotactic procedures. The safety and efficacy of the stereotactic procedure is determined by two major factors: (1) meticulously monitoring the electrode insertion path, without damaging critical brain tissue; and (2) the ability to reach the STN with high precision (<2 mm) The robot is designed: i) to be compact so that the robot body can be fixed on the patient's skull properly within the tight dimensional constraints given by the head coil; ii) to enable automatic trajectory planning and instrument alignment; iii) to perform bilateral manipulation independently; and iv) to fulfill the MRI compatibility with ASTM F2503 standards, by ensuring no magnetic components are involved in the robot platform. In general, the robot's operation will not induce noticeable image artifacts or significant reduction in signal-to-noise ratio (SNR) within the imaging region-of-interest (ROI).

Embodiments of the subject invention provide a compact design that enables the robot to bilaterally operate within the constrained space of a standard imaging head coil. MR safe, high-performance hydraulic transmissions are incorporated, in which the working media can be pre-loaded and high transmission stiffness can be ensured. Sufficient targeting accuracy has been demonstrated in a simulated needle insertion task of deep brain stimulation (DBS). An MR-based tracking technique is adopted and capable offering real-time and continuous (30-40 Hz) 3-dimensional localization of the robotic instrument under a proper MR tracking sequence. This technique outperforms the conventional methods of using low-contrast passive fiducials that can only be revealed in the MR image domain. Wireless tracking units/markers, which can be integrated with the robot, can be utilized and comprise miniaturized coil circuits fabricated on flexible thin films. A navigation test has been performed under the standard MRI settings in order to visualize the 3-dimensional localization of the robot instrument. MRI-compatibility test has proved the minimal interference to MR images of the presented hydraulic robotic platform.

Embodiments of the subject invention include the following development of the first intra-op MRI-guided robot capable of performing bilateral neuro-stereotaxy based on a single anchorage on the patient skull. Navigation for both bilateral targets can be performed independently and simultaneously. The light-weight and compact robot is designed to operate within the confined workspace of an MR imaging head coil. The robot can be actuated by a set of high-performance hydraulic transmissions which are MR safe/induce minimal imaging artifacts. An MRI-guided navigation can be incorporated and utilize wireless MR-based tracking coil units, offering real-time positional feedback directly in MR image coordinates. This avoids any process of offline registration between coordinates of the tracking and imaging space.

The robot can be implemented in regular diagnostic MM facilities without having to transfer a patient, scanner or instruments during the procedure. It also allows neurosurgeons to remotely operate the surgical (e.g. DBS) tools in a control room. This inhibits the patients and clinicians from exposure to potentially harmful radiation. This maintains smooth surgical workflow, and also enables ease of communication between radiologists and assistants in the same room.

DETAILED DESCRIPTION

Figure 3:
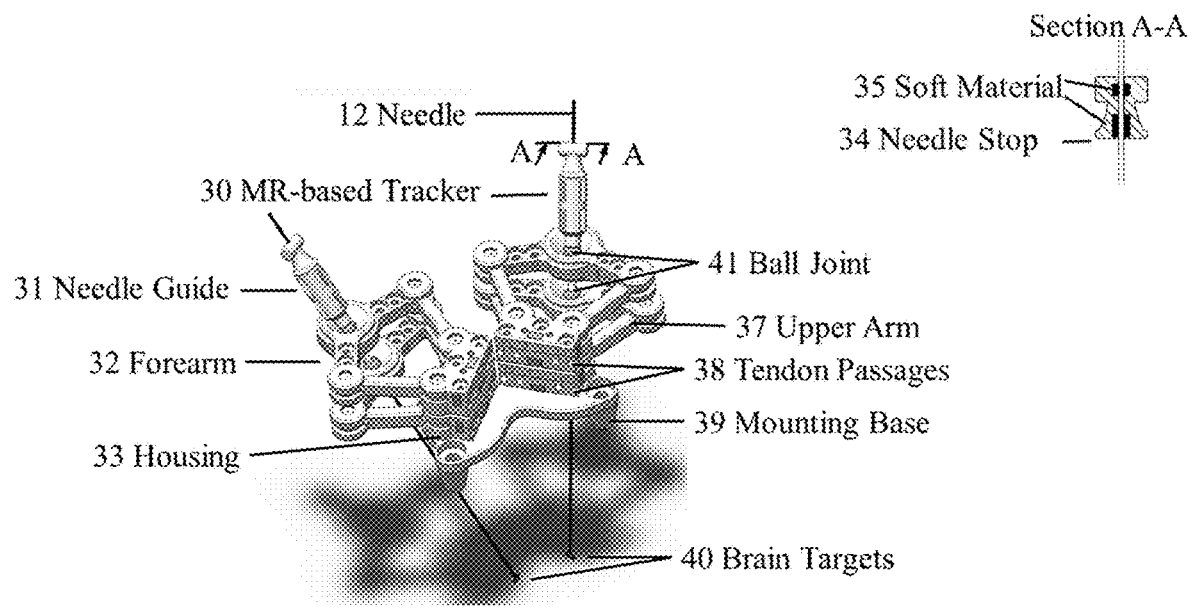
FIG. 3 is a diagram illustrating the mechanism of bilateral stereotactic manipulators.

Embodiments of the subject invention are designed to perform bilateral instruments navigation. In one embodiment, the present invention is for MRI guided deep brain stimulation (DBS) during the intraoperative phase of surgery. A CAD model and components of the proposed robotic manipulator are illustrated in FIG. 3. The parallel mechanisms possess advantages in positioning accuracy and stiffness. The robot's planar position is controlled by two actuated rotational joints and three passive ones. The design enables two manipulators each with 4 degrees of freedom, double-layer five-bar-linkage in a bilateral setting.

The manipulator comprises at least one rigid arm, at least one housing, and at least one mounting base affixed to a skull via at least one mounting unit, preferably bone screw. All anchorage sites are away from the sagittal suture to avoid the possible trauma to the critical structures underneath. In an embodiment of the subject invention, the lowest surface of the arms can be approximately 20-30 mm above the Burr hole, depending on the patient-specific skull curvature and its anchorage site (see, for example, FIG. 4). This exposure space at the entry point is reserved for surgeon's observation. For versatility, the mounting base can be tailor-made for a patient based on the pre-op images. All the housings can be manually plugged onto and fixed with the mounting base. Slots on the surface are reserved for the attachment of registration markers. Passages are also created to allow fixture of the sheath's end for better tendon routing. The revolute joints inside the housing can be therefore actuated by the tendons. Two ball joints are incorporated at the distal end of the forearms. A needle guide is oriented by these two joints, and axially fixed with the upper one. Prior to inserting the needle through the cannula held by both end-effectors of the double-layer manipulators, the allowable insertion depth can be preset by the needle stop. Soft material is also embedded inside the cannula/needle stop so as to limit the needle linear motion by inducing the sliding friction.

Figure 7:
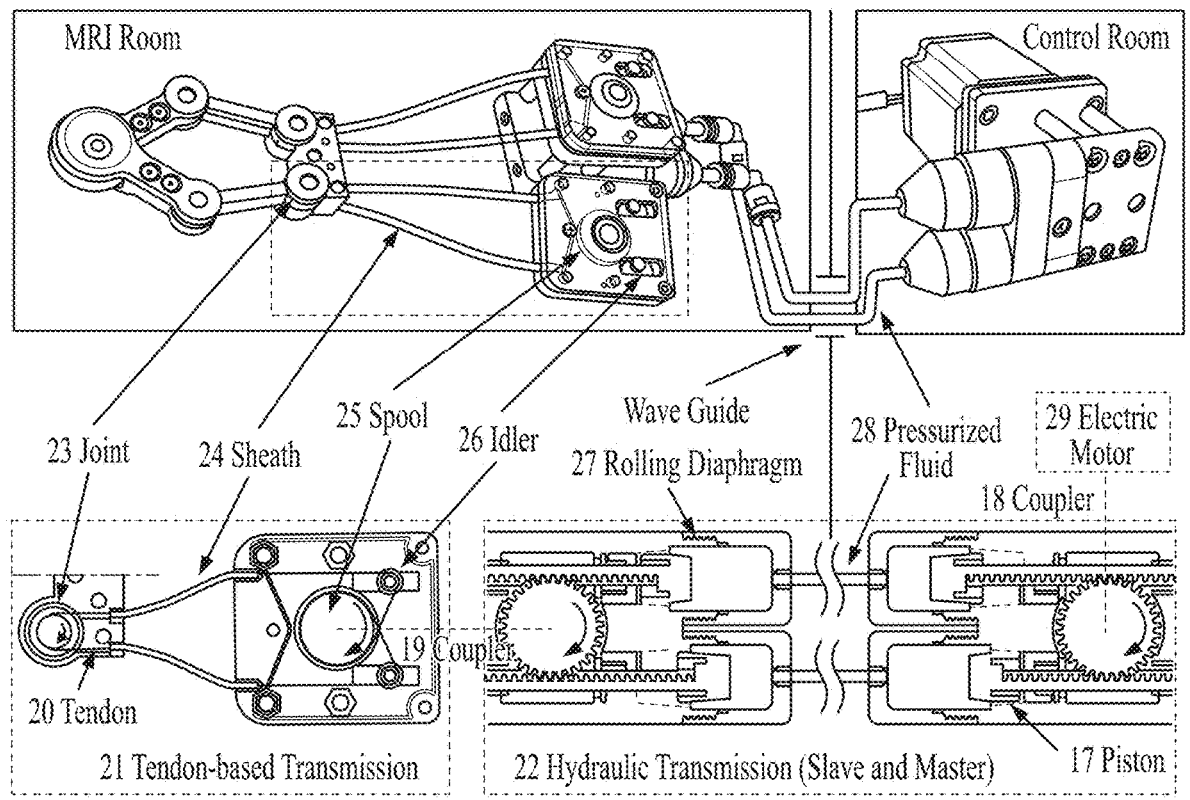
FIG. 7 is an image and schematic diagram of a 1-Dof actuation design.

Short-tendon-driven design is adopted with the aim to reach stringent criteria, in terms of not only the spatial constraints imposed by the head coil, but also the weight that may cause discomfort to the patient. FIG. 7 shows a slave manipulator in the MRI room, which is wired with a pair of hydraulic transmission units 22 connecting with the other pair in the control room. Such a compact design of the slave can minimize the motion inertia and facilitate manipulation flexibility across the constrained workspace. It is still capable of applying a promising level of torque/force generated by the hydraulic motor. The components can be fabricated by 3D-printing and/or be comprised of polymers.

For a 1 degree of freedom actuation, as depicted in FIG. 7, the manipulator base joint and the hydraulic units can be separated by <200 mm and connected with one loop of thin tendons tightly channeled through the sheaths 24. The sheath material is axially-incompressible to inhibit sudden/excessive pulling force applied on the skull. It also supports the route of tendon with sufficient pliability even under the high tensile strength. The tendon-sheath friction can be reduced by proper lubrication. Two idlers 26 can also be used to pre-load the tension in order to reduce any mechanical backlash.

The master (which can be located in a control room) and slave (which can be location in an MRI room) actuation system can include two identical linear-to-rotation mechanisms (see, for example, FIG. 7). The hydraulic power originates from an electric motor 29 and is transmitted via a pair of semi-rigid long pipes. These design parameters are of importance to the performance of transmission dynamics. It is suggested that using pipes with shorter length and larger diameter can reduce the fluid friction, transmission latency and energy loss. The pipes can be filled with incompressible liquid 28 (e.g. water) and are passed through the waveguide in between two rooms. The liquid pressure can be preloaded to push the piston 17 towards the pinion-and-rack gear, keeping their teeth in steady contact without backlash.

Seals, including rolling-diaphragms 27 are used to seal the cylinders and result in negligible sliding friction during transmission. The wall of the diaphragm 27 can be reinforced with fabric for high fluid pressure. The resultant transmission response and power efficiency can outperform conventional hydraulic sealing with O-rings, of which the sliding friction is significant.

Figure 1:
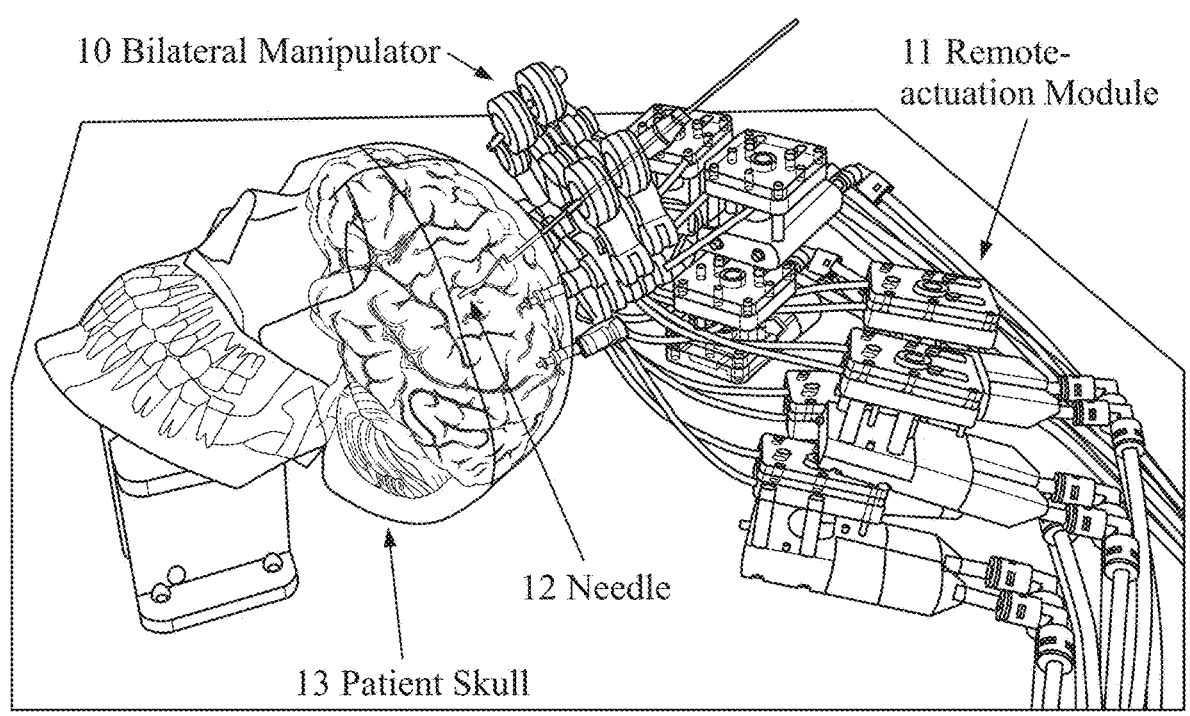
FIG. 1 is an image of an MRI compatible robot for intra-operative MRI-guided bilateral stereotactic neurosurgery.
Figure 2A:
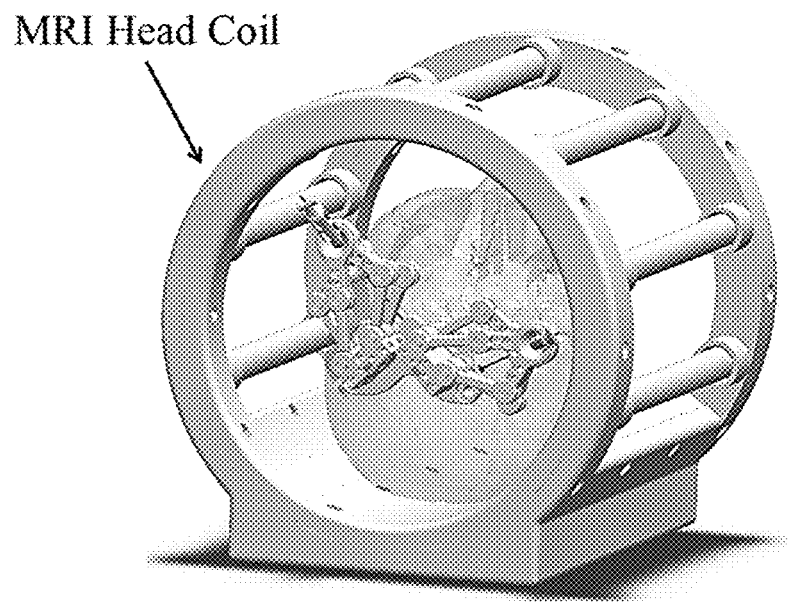
FIG. 2a is a diagram illustrating two (bilateral) manipulators attached on skull and fully stretched in two extreme configurations within the confined space of an MRI head coil.
Figure 2B:
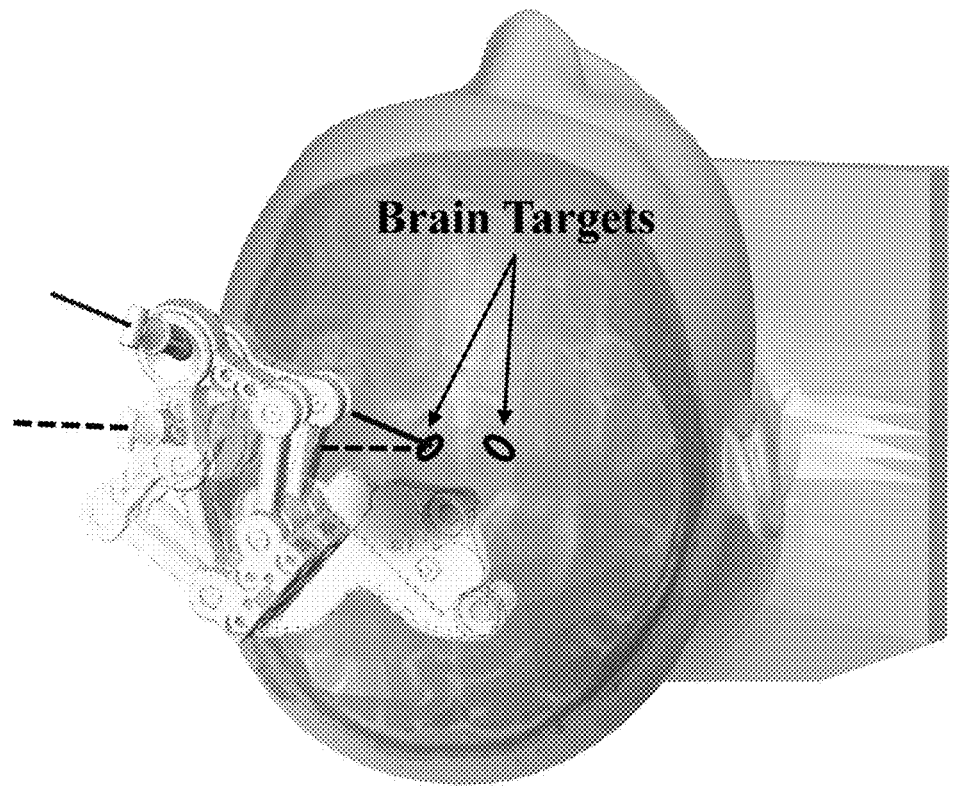
FIG. 2b is a diagram illustrating a single manipulator targeting the brain target with two possible configurations.
Figure 4:
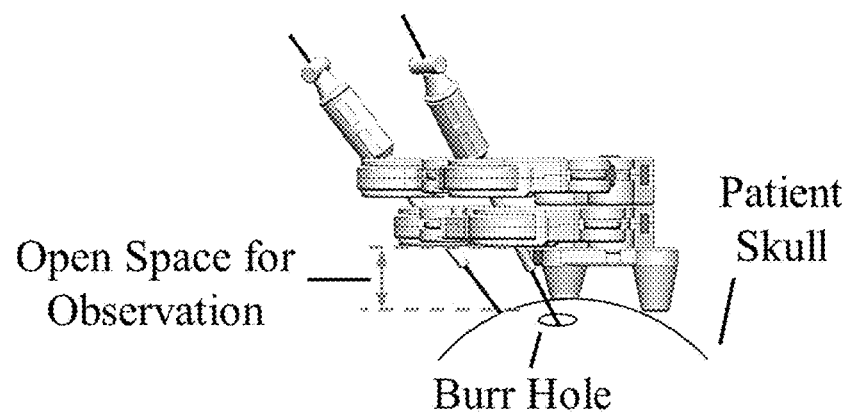
FIG. 4 is a diagram illustrating a sagittal view of bilateral stereotactic manipulators.

CAD models and components of an embodiment of the subject invention are illustrated in FIGS. 2-4. Parallel mechanisms possess advantages in positioning accuracy and stiffness. The planar position is controlled by two actuated rotational joints and three passive joints. This design results in two 4 degrees of freedom, double layer, five-bar-linkage manipulators in a bilateral setting. In one embodiment, a manipulator comprises rigid arms, four housings 33, and a mounting base 39 affixed to the skull via four bone screws, two at each side. The anchorage sites are positioned apart from the sagittal suture to avoid possible trauma to the patient. The mounting base 39 can be tailored to a specific patient. The housings 33 can be manually plugged onto and fixed with the mounting base 39. The surface can be reserved for attaching registration markers. Passages 38 can be created to allow fixture of the sheath's end for better tendon routing. The revolute joints inside of the housing can be actuated by the tendons. Two ball joints 41 can be incorporated at a distal end of the forearms 32. A needle guide 31 can be orientated by these two joints and axially fixed with the upper joint. Prior to inserting a needle 12 through a cannula, the allowable insertion depth can be preset by a needle stop 34. Soft material 35 can also be embedded inside the cannula to limit the linear motion of the needle 12 by inducing sliding friction.

Figure 5:
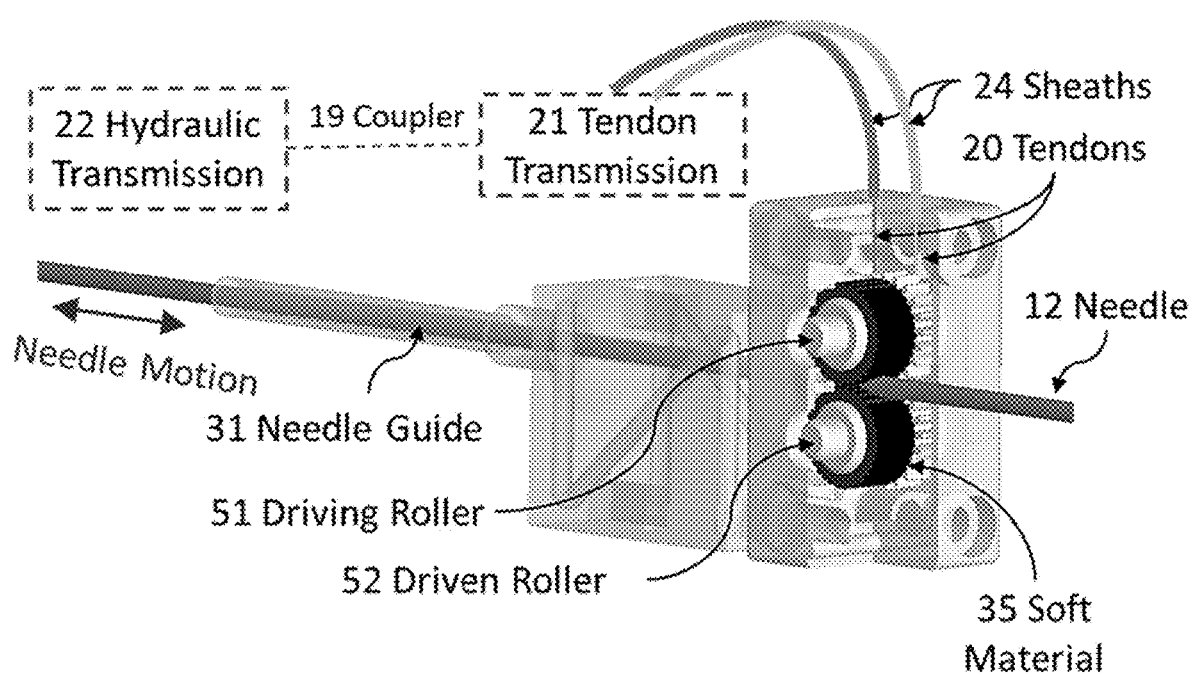
FIG. 5 is a diagram illustrating a linear actuator incorporated with needle guide for needle insertion.

To automatically insert the needle, a linear actuator can be incorporated to the needle guide. It can be driven by the similar master-slave actuator mechanism (see, for example, FIG. 5). Needle guide constrains the needle in translational motion. A friction drive composed of rollers can be employed, with one powered (driving roller) and the other one passively driven (driven roller). The high friction is ensured by the rough surface of soft material enclosing the rollers. They can both rotate inwards or outwards for inserting or retrieving the needle. The distance between two roller axes is smaller than the outer diameter of the soft roller, so as to maintain radial pushing forces against each other and increase the gripping force for the needle. Tendons are connected to driving roller while the remaining parts of slave actuator can be all placed on the surgical table.

In an embodiment of the subject invention, a surgical robot comprises two manipulator mounted upon a single mounting base. As seen in FIG. 3, two manipulators are positioned on the mounting base 39 to permit simultaneous and independent bilateral operations. Each manipulator comprises a tendon-based lower actuator and a tendon-based upper actuator stacked on top of the lower actuator. The mounting base 39 can be connected to the housing 33 of each lower actuator. The housings 33 of the upper and lower actuators can each have tendon passages 38 to permit tendons to pass through and actuate two rotational joints for each actuator. Each rotational joint can be connected to a proximal end of an upper arm 37. The distal end of each forearm can be connected to a passive joint. Each passive joint can be connected to a forearm 32 and the two forearms 32 of each actuator can be connected together with a ball joint 41. A needle guide 31 can be inserted into the ball joints 41 of the upper and lower actuators. A needle can be inserted, by hand and/or linear actuator, into the needle guide 31 and fitted with a needle stop 34 to assist during surgery. An MR-based tracker 30 can be embedded into the needle guide 31. The mounting base 39 can be affixed to a skull via four bone screws with two for each side of the mounting base 39.

Figure 6:
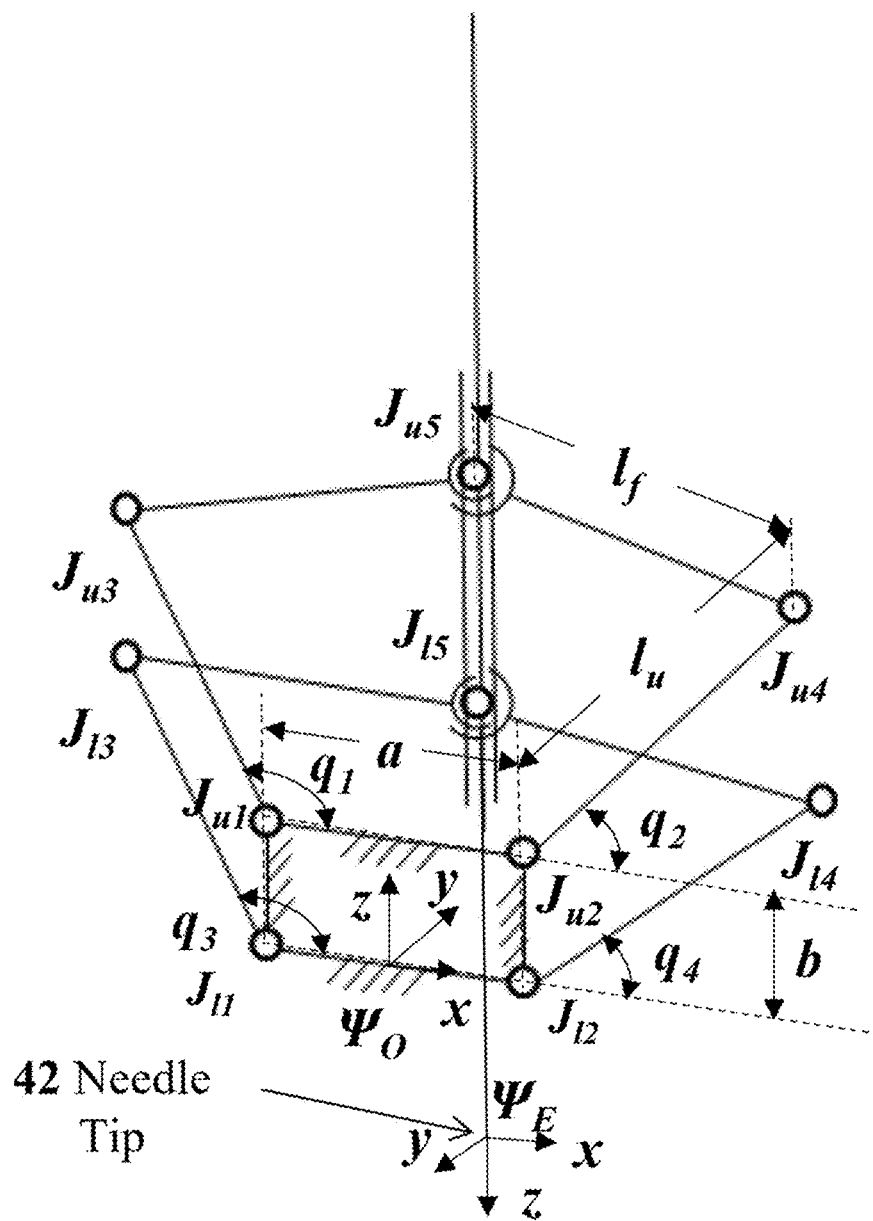
FIG. 6 is a kinematic diagram of a single manipulator with coordinate frames $\psi_o$ and $\psi_E$ defined at the housing base and needle tip, respectively.

FIG. 6 depicts a kinematic diagram of one double layer manipulator. Two coordinate frames $\psi_o$ and $\psi_E$ are defined at the housing base and needle tip, respectively. The cannula is connected by two passive joints $J_{u5}$ and $J_{l5}$ from upper and lower layers, respectively, the cannula's position can be manipulated by independent (x-y) planar motion of the upper and lower layers containing the points $P_{uk}$ and $P_{lk}$, respectively. These points denote 2D coordinates of corresponding joints $J_{uk}$ and $J_{lk}$ for k=1, 2, 3, 4, which can be solved by the following equation sets:

$$\begin{cases} \|p_{u3} - p_{u5}\| = l_f \\ \|p_{u4} - p_{u5}\| = l_f \end{cases} \text{ and } \begin{cases} \|p_{l3} - p_{l5}\| = l_f \\ \|p_{l4} - p_{l5}\| = l_f \end{cases} \quad (1)$$

Horizontal offset a separates two actuated joints and vertical offset b separates the upper and lower layers. The array of the actuated joints can be defined as $q=[q_{u1}, q_{u2}, q_{u3}, q_{u4}]^T$ two types of singularities can be found in this five-bar linkage mechanism. The first occurs when the forms are colinnear (e.g. joints $J_{l3}$, $J_{l4}$, $J_{l5}$, are in one line), and the second occurs when only when the arms are fully stretched. To inhibit collineation of the pairs of forearms, a mechanical limit on the relative rotation can be utilized. For instance $J_{l5}$ can always be located outside the quadranngle area of $J_{l1}$, $J_{l2}$, $J_{l3}$, and $J_{l4}$. To resolve inverse kinematics, the needle's orientation can be denoted by the unit $\tau^+$ and be denoted as:

$$\vec{r} = \frac{p_{l5} - p_{u5}}{\|p_{l5} - p_{u5}\|} \quad (2)$$

Assume the insertion depths, $d_u$ and $d_l$, define linear distance from join $J_{u5}$ and $J_{l5}$, respectively to the brain target. The position of needle tip 42, $p_e$, acting as the uitmate end effector of both manipulators can be calculated as:

$$p_e = p_{u5} + d_u \cdot \vec{r} \quad (3)$$

By way of example, to find the four actuated joint angles, $q=[q_{u1}, q_{u2}, q_{u3}, q_{u4}]^T$, based upon the desired needle position with respect to the MR image coordinates, coregistration between the robot and the image coordinate system is required. The calculated parameters (ie. $p_e$ and $\vec{r}$) can be defined in $\psi_o$. Coordinate $p_{u5}$ and $p_{l5}$ can be found be calculating the crossing points of the needle and two layers using the line equations:

$$p_{u5} = p_e - d_u \cdot \vec{r} \text{ and } p_{l5} = p_e - d_l \cdot \vec{r} \quad (4)$$

Coordinates $p_{uf}$ and $p_{lf}$ belong to the triangle $\Delta J_{u1}, J_{u3}, J_{u5}$ and $\Delta J_{l1}, J_{l3}, J_{l5}$, respectively, Angles $\angle J_{u3} J_{u1}J_{u5}$ and $\angle J_{u4} J_{u2}J_{u5}$ (denoted as $\theta_{u1}$, $\theta_{u2}$) can be solved using cosine law, respectively, in triangles $\Delta J_{u1}, J_{u3}, J_{u5}$ and $\Delta J_{l2}, J_{l4}, J_{l5}$ by the following expressions:

$$l_f^2 = l_u^2 + \|p_{u5} - p_{u1}\|^2 - 2l_u\|p_{u5} - p_{u1}\|\cos\theta_1 \quad (5)$$

$$l_f^2 = l_u^2 + \|p_{u2} - p_{u5}\|^2 - 2l_u\|p_{u2} - p_{u5}\|\cos\theta_1 \quad (6)$$

To avoid the second type of singularity joints $J_{u3}$, $J_{u4}$, for example can be positioned beyond triangle $\Delta J_{u1}, J_{u3}, J_{u5}$, such that $q_{u1}=\theta_{u1}+\alpha_{u1}$ and $q_{u2}=\pi-(\theta_{u2}+\alpha_{u2})$. It should be appreciated by one of ordinary skill in the art that other actuation parameters can be solved with a similar process.

Figure 8A:
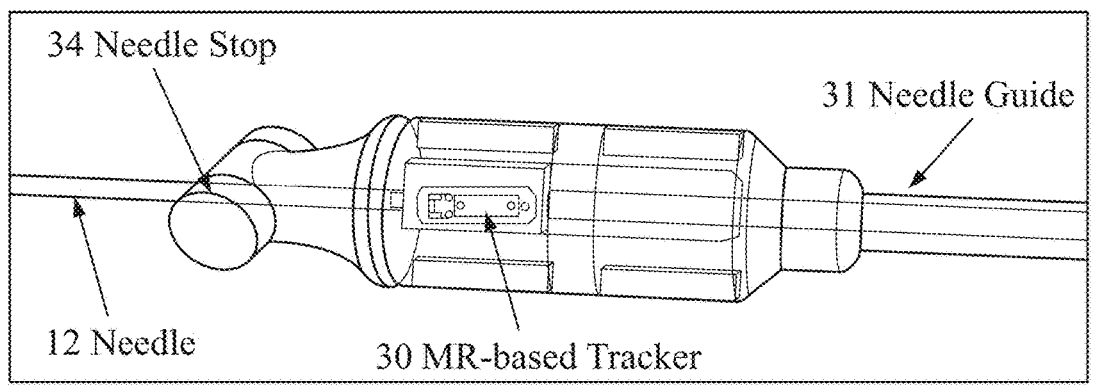
FIG. 8a is an image of the needle guide embedded with MR-based trackers.
Figure 8B:
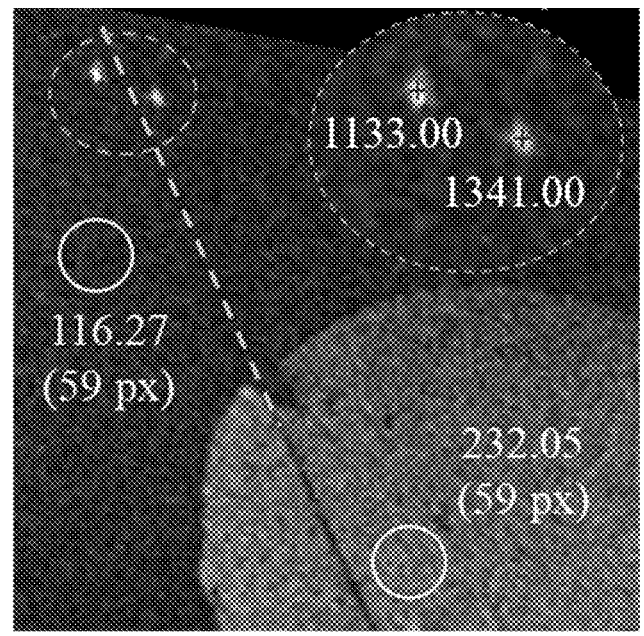
FIG. 8b is an MR image of the brain phantom (in coronal view) revealing the two tracking markers by corresponding bright spots.
Figure 8C:
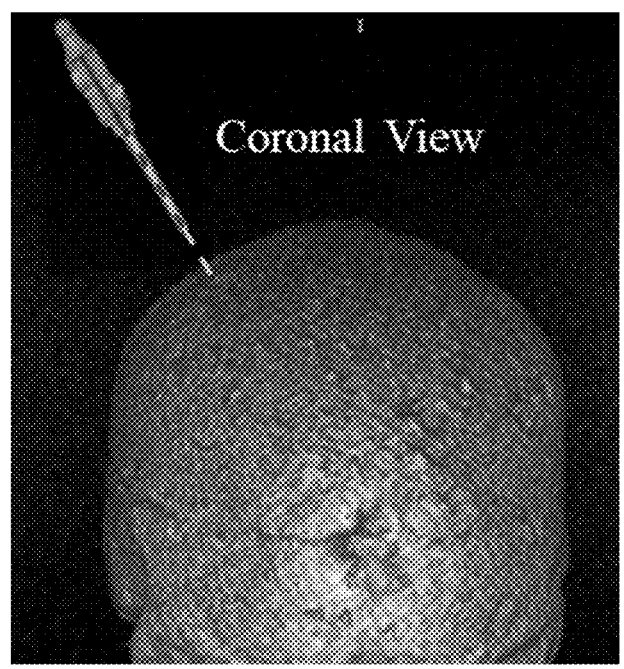
FIG. 8c illustrates the virtual configurations of the instrument augmented on the high-contrast markers in coronal view.
Figure 9:
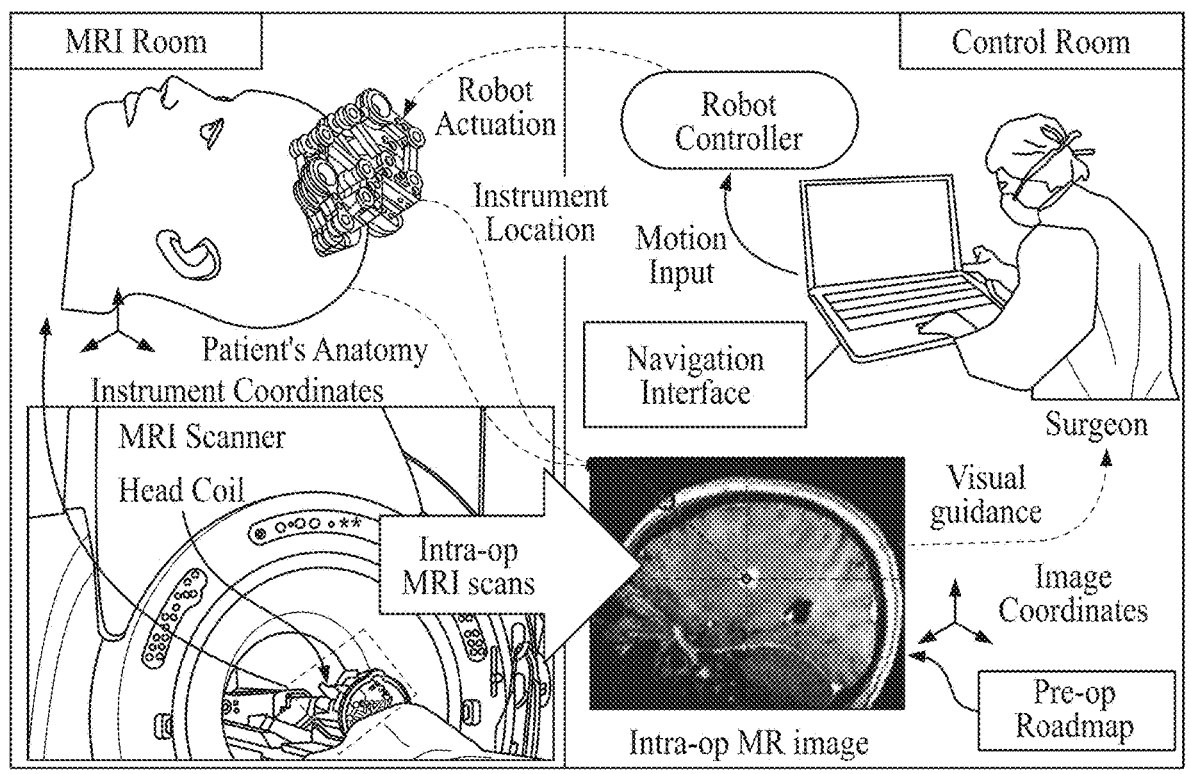
FIG. 9 is a system schematic illustrating the MRI-guided robot-assisted stereotaxy.

MR-based wireless tracking is first introduced to such robotic stereotaxy (see, for example, FIG. 8). FIG. 9 illustrates the system setup for MRI-guided robotic stereotaxy. Two or more trackers 30 can be embedded in the needle guide 31 (FIG. 8a). Soft hollow rings injected with MRI-visible liquid can be attached to the burr holes for localization of entry points and immediate trajectory planning. 3D spoiled gradient recalled-echo (SPGR) sequence can be used to assess the location and orientation of the needle guide. The needle can be then inserted and scanned with the same imaging sequence. FIGS. 8b and 8c show the resultant MR image and 3D reconstruction in coronal view. Both the trackers and the inserted needle can be visualized. The signal intensities of two trackers are in the high contrast to those of background and brain phantom. This contrast can be further enhanced by dedicated excitation at lower flip angles (e.g. 1°), which can minimize the background signals.

Figure 10:
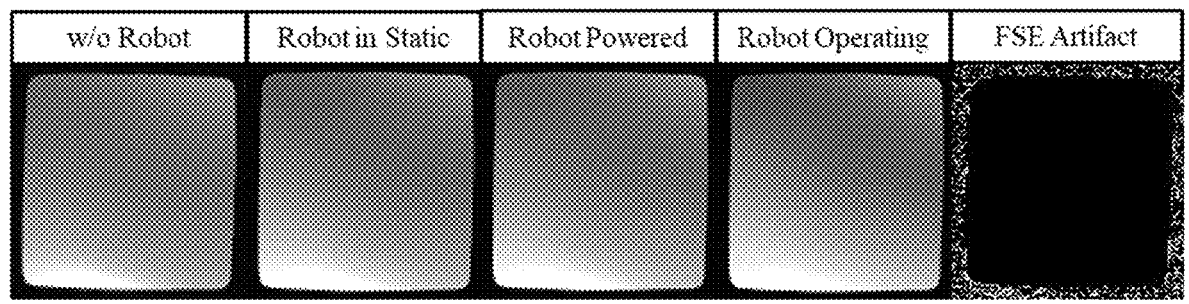
FIG. 10 are MRI images of a signal-to-noise ratio phantom under T2-weighted fast spin echo sequence, when the robot is placed at an isocenter and operated under different conditions.

FIG. 10 illustrates MRI images of the phantom under fast spin echo sequence when the robot is placed at an isocenter beside the phantom and operated under different conditions. The first condition is "w/o robot", i.e. only the phantom is placed in the scanner. The second condition is "robot in static", i.e. the robot has been introduced into the scanner, but all of the power is off. In the third condition, which is "robot powered", the electric power is on, but the robot is static. The fourth condition is "robot in motion," which is when the robot is in its normal operation state. The images corresponding to the two conditions, baseline and robot operating, are compared. Pixels with intensity that varied by 30% or above were considered as artifacts. These artifacts would appear as white pixels in the binary map. No artifact was observed within the phantom area. As defined by the ASTM standard, it indicates the operation of robot generated zero artifact.

In an embodiment of the subject invention, a robot can comprise two manipulators mounted above two Burr holes created in a skull. Each manipulator can provide 4 degrees of freedom manipulation on the instruments access to each corresponding Burr hole, including pitch, roll, and offsets along the x-y plane above the skull surface. This facilitates alignment of a desired straight line trajectory to the brain target.

To facilitate bilateral stereotactic manipulation, embodiments of the subject invention can be designed: i) to be compact so the robot can be fixed on a skull within tight dimensional constraints due to a head coil, ii) to enable automatic trajectory planning and instrument alignment, iii) to perform bilateral manipulation independently, and iv) to fulfill MRI compatibility with the ASTM F2503 standard, be enduring no magnetic components are involved in the robot platform. In general, the robot will not induce noticeable artifacts or significant reduction in signal-to-noise ratio (SNR) within the region-of-interest (ROI).

FIG. 12 illustrates the workflow of conventional and MRI-guided robot-assisted stereotactic neurosurgery. Targeting errors, in terms of patient position, registration and brain shift, can be eliminated through the real-time MRI guidance and robotic manipulation. The procedure time can be significantly reduced, as well as the surgical cost. It may involve MRI scans, the use of robot/MRI-compatible instruments and the extra manpower for robot operation.

Figure 12A:
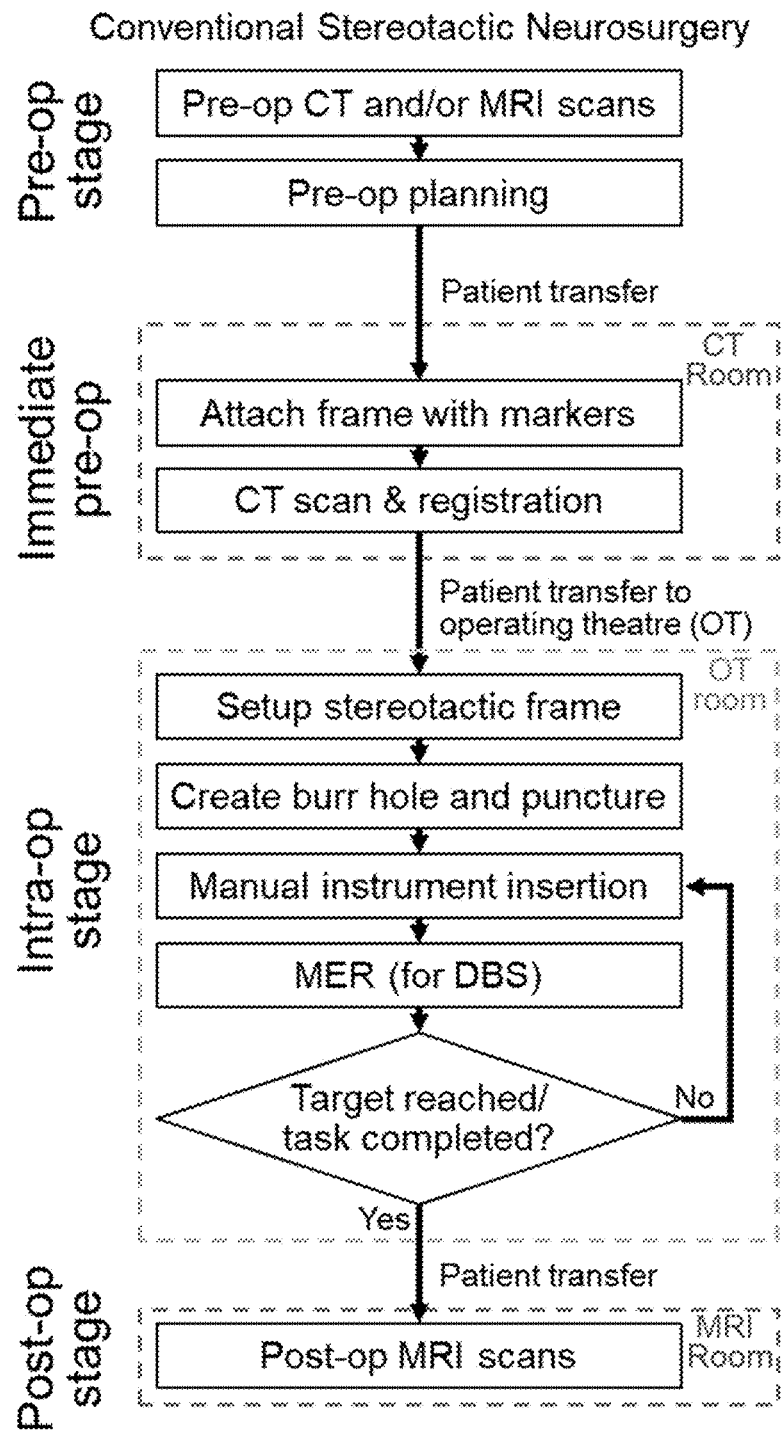
FIG. 12a illustrates the surgical flow of conventional stereotactic neurosurgery.

FIG. 12a illustrates a possible surgical flow of conventional stereotactic neurosurgery. Conventional surgical operations can be divided into a preoperative, an intraoperative, and a postoperative phase. The immediate preoperative phase can occur between the preoperative and intraoperative phase. During the preoperative phase the medical staff can conduct both a physiological and a psychological assessment of a patient by performing an MRI, computerized tomography (CT) scanning, blood testing, and addressing any anxieties a patient may have. The medical staff can additionally devise a plan to best reach a desirable outcome of the surgery.

During an immediate preoperative phase, a stereotactic frame can be attached to the head of a patient along with markers. A CT scan of the patient wearing the stereotactic frame can be performed and registration between the CT scan image and any intraoperative tool positions can be performed. Afterwards the patient can be transferred to the operating room or operating theatre.

During the intraoperative phase, the medical staff can set up the stereotactic frame on the patient's head. A Burr hole can be drilled or scrapped into the patient's skull. A needle can be manually inserted into the patient's brain through the Burr hole. If the patient is undergoing deep brain stimulation, a microelectrode can be implanted to monitor an electrical response to the stimulation. If the desired objective has been reached, the needle can be removed and the Burr hole sealed. If, however, the desired objective has not been reached, the needle can be reinserted and the process repeated.

After the surgery is complete, the patient can be transferred out of the operating room and monitored for any post-surgery effects. MRI scans can be conducted during a postoperative phase and the medical staff can determine if any additional treatment is necessary.

Figure 12B:
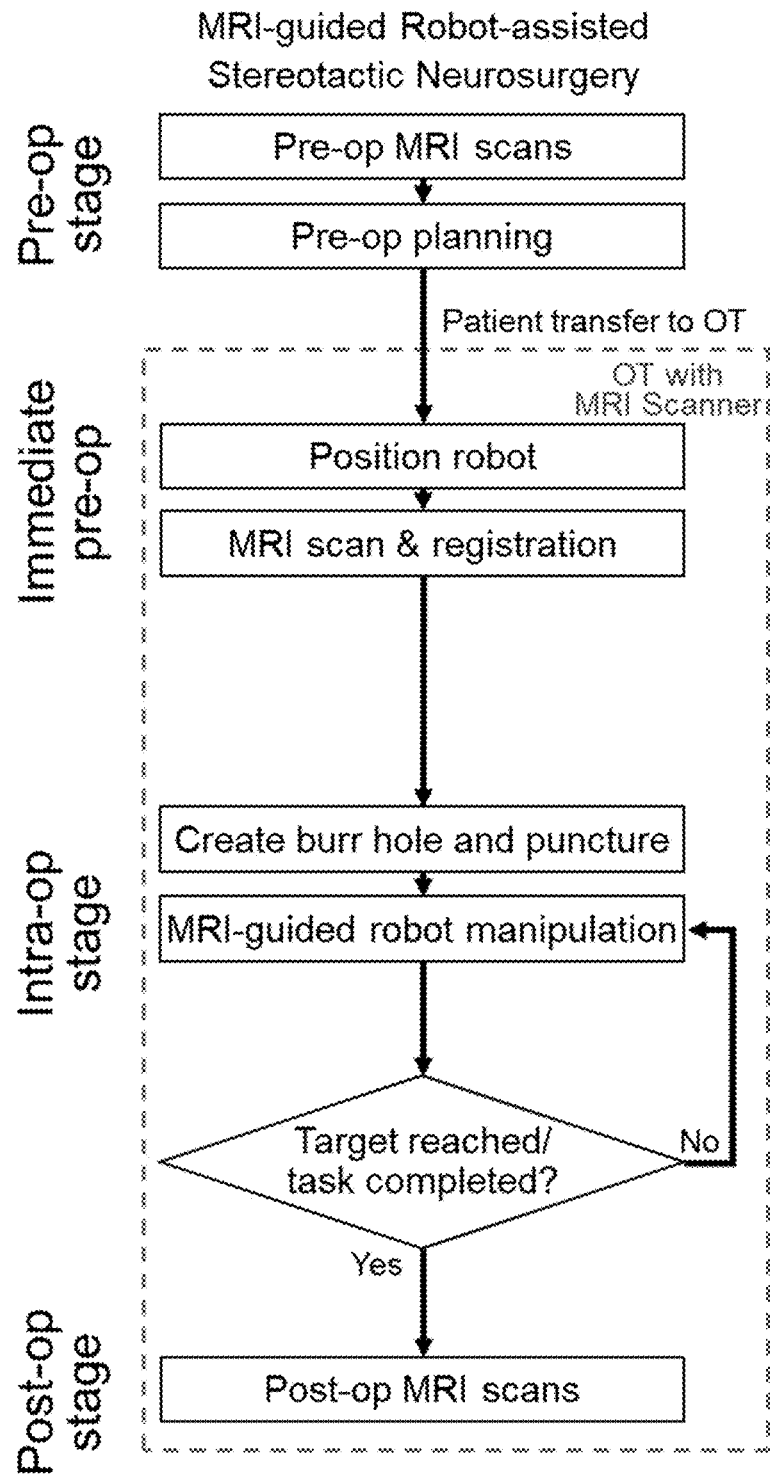
FIG. 12b illustrates the surgical flow of MRI-guided robot-assisted stereotactic neurosurgery.

FIG. 12b illustrates the surgical flow of MRI-guided robot-assisted stereotactic neurosurgery. The preoperative phase is similar to the conventional stereotactic neurosurgery preoperative phase. After the preoperative phase, the patient can be transferred to the operating room. The MRI guided robot can be affixed to patient's skull with screws. An MRI scan can be performed and the MRI image can be registered with a robotic coordinate system. The medical staff can create one or more Burr holes in a patient's skull. A surgeon can use MRI-based tracking and images to guide the needle in the patient's brain by manipulating each actuator of the robot. If the desired objective has been reached, the needle can be removed and the Burr hole sealed. If, however, the desired objective has not been reached, the needle can be reinserted and the process repeated. After the surgery is complete, the patient can be transferred out of the operating room and monitored for any post-surgery effects. MRI scans can be conducted during a postoperative phase and the medical staff can determine if any additional treatment is necessary.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1. A surgical robot for magnetic resonance imaging guided interventions, comprising:
- a manipulators comprising a tendon-based upper actuator and tendon-based lower actuator;
- a mounting base connected to the lower actuator;
- a needle guide; and
- a needle disposed within the needle guide;
- wherein each actuator comprises:
  - a housing with a plurality of openings to allow a tendon to pass through,
  - two rotational joints connected to the housing,
  - two upper arms connected to the two rotational joints, respectively,
  - two forearms connected to the two upper arms, respectively, at a proximal end of each forearm by a passive joint,
  - a passive ball joint connecting the two forearms at the distal end of each forearm,
  - wherein the needle guide is disposed within the ball joint of the upper actuator and of the lower actuator, and
  - wherein the mounting base has a plurality of screw holes for bone mounting.

Embodiment 2. The surgical robot of embodiment 1, further comprising a needle stop and/or a linear actuator disposed on the needle.

Embodiment 3. The surgical robot of any of embodiments 1-2, further comprising one or more MR-based trackers disposed on the needle guide.

Embodiment 4. The surgical robot of any of embodiments 1-3, wherein the robot includes a plurality of manipulators.

Embodiment 5. The surgical robot of any of embodiments 1-3, further comprising:
- two tendons inserted into the housing of the upper actuator;
- two tendons inserted into the housing of the lower actuator; and
- two or more spools connected to each tendon, respectively,
- wherein each tendon is connected to each rotational joint of each housing, respectively.

Embodiment 6. The surgical robot of embodiment 5, wherein each tendon is channeled through a sheath, respectively.

Embodiment 7. The surgical robot of embodiment 6, further comprising:
- a first set comprising a plurality of pinion gears and rack gears,
- wherein each pinion gear of the first set is coupled to each spool, respectively; and
- a plurality of hydraulic tubes, each tube connected at a first end to each rack gear, respectively, and filled with fluid,
- wherein the fluid and each rack gear of the first set are separated by a rolling diaphragm.

Embodiment 8. The surgical robot of embodiment 7, further comprising:
- a second set comprising a plurality of pinion gears and rack gears,
- wherein each pinion gear of the second set is coupled to a motor,
- wherein each rack of the second set is connected to an opposite end of each hydraulic tube, respectively, and
- wherein the fluid and each rack gear of the second set are separated by a rolling diaphragm.

Embodiment 9. The surgical robot of any of embodiment 1-8, wherein the surgical robot is mounted on a skull.

Embodiment 10. The surgical robot of any of embodiments 1-9, wherein the needle is a rigid straight surgical instrument, e.g. DBS needle.

Embodiment 11. A surgical robot for magnetic resonance imaging guided interventions, comprising:
- two manipulators, each manipulator comprising a tendon-based upper actuator and a tendon-based lower actuator;
- each lower actuator connected to a mounting base;
- two needle guides; and
- two needles, each needle disposed within a respective needle guide,
- wherein each actuator comprises:
  - a housing with a plurality of openings to allow a tendon to pass through,
  - two rotational joints connected to the housing,
  - two upper arms connected to the two rotational joints, respectively,
  - two forearms connected to the two upper arms, respectively, at a proximal end of each forearm by a passive joint, and
  - a passive ball joint connecting the two forearms at the distal end of each forearm;
- wherein one of the needle guides is disposed within the ball joint of both the upper actuator and the lower actuator of each manipulator, respectively, and
- wherein the mounting base has a plurality of screw holes for bone mounting.

Embodiment 12. The surgical robot of embodiment 11, further comprising two needle stops and/or two linear actuators, each needle stop/linear actuator disposed on a respective needle.

Embodiment 13. The surgical robot of any of embodiments 11-12, further comprising two or more MR-based trackers, each MR-based tracker disposed on a respective needle guide.

Embodiment 14. The surgical robot of any of embodiments 11-13, further comprising:
- two tendons inserted into the housing of each upper actuator;
- two tendons inserted into the housing of each lower actuator; and
- two or more spools connected to each tendon, respectively,
- wherein each tendon is connected to each rotational joint of each housing, respectively.

Embodiment 15. The surgical robot of embodiment 14, wherein each tendon is channeled through a sheath, respectively.

Embodiment 16. The surgical robot of any of embodiments 11-15, further comprising:
- a first set comprising a plurality of pinion gears and rack gears,
- wherein each pinion gear of the first set is coupled to each spool, respectively; and a plurality of hydraulic tubes, each tube connected at a first end to each rack gear, respectively, and filled with fluid, wherein the fluid and each rack gear of the first set are separated by a rolling diaphragm.

Embodiment 17. The surgical robot of any of embodiments 11-16, further comprising:

a second set comprising a plurality of pinion gears and rack gears, wherein each rack of the second set is connected to an opposite end of each hydraulic tube, respectively, and wherein the fluid and each rack gear of the second set are separated by a rolling diaphragm.

Embodiment 18. The surgical robot of any of embodiments 11-17, wherein the surgical robot is mounted on a skull.

Embodiment 19. The surgical robot of any of embodiments 11-18, wherein the needles are straight rigid surgical instruments, e.g. DBS needles.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1—Transmission Stiffness

An iterative test was conducted on a 1 degree of freedom actuation. The upper arms of the manipulator were fixed such that rotation of the actuated joint was constrained. Ten meter pipes filled with distilled water were used to connect the master-to-slave hydraulic units. The master unit was actuated by an electrical DC motor that provided 500 encoding pulse feedback. The DC motor was also geared down in ration 14:1, generating rotary resolution of 0.052°. A torque sensor with 5 m/Nm sensitivity was used to measure the external load. The tests were under a bi-directional load. The transmission fluid in the pipes was preloaded at 0.5, 1.0, 1.5, and 2.0 bars in order to investigate the transmission stiffness varying with different fluid pressure levels. The external loads were gradually increased, while recording the corresponding piston displacements.

Figure 13:
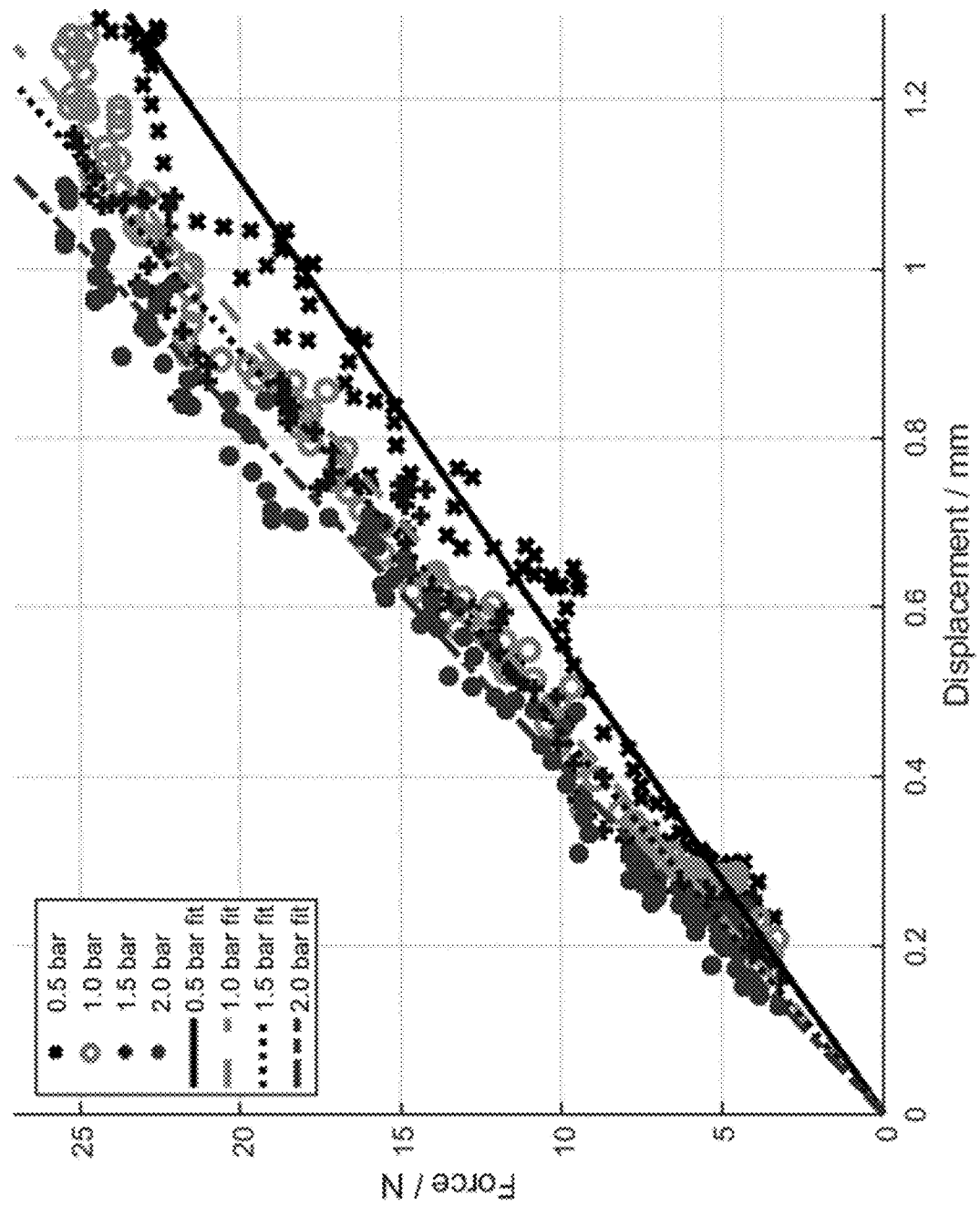
FIG. 13 is a plot of force displacement showing the transmission stiffness of an actuation module at four pre-loading levels.

The force displacements diagram, as seen in FIG. 13, shows the increasing trend of transmission stiffness with higher preloaded fluid pressure. This can be attributed to the enhanced Teflon material stiffness of the hydraulic pipes upon the increased load. The data was linearly fitted using least-square regression, which indicates the maximum stiffness coefficient can reach 24.35 N/mm under 2 bar preloaded pressure.

Example 2—Needle Targeting Accuracy

An EM positional tracking system was used to measure the 3D coordinate of any point defined in the experimental setup. Ten points were simulated as the STN target, five in each side on a plastic plate. The points were roughly 100 mm below the lower layer manipulators. This is the typical depth of a stereotactic target beneath a skull. These measured target coordinates were registered with the robot coordinate system. Two EM tracking coils were attached to one robot forearm, one on each layer. A phantom needle with similar diameter to a DBS cannula was used in this targeting task. The exact needle tip position and orientation were calculated by two 5 degrees of freedom coils fixed at the needle's tip.

Configurations of the robot and needle guide, along with needle insertion depth, were measured and calculated. After aiming at the target points, the needle was inserted manually. The proximal distance from the needle tip to the target and the distance from the target to the needle axis were measured. The trials were repeated for needle insertion for five targets on each side. The targeting accuracy was quantified by mean error and its standard deviation and shown in Table 1.

TABLE 1

Needle Targeting Accuracy Test

| Side | Needle tip | | Normal to the needle | |
|---|---|---|---|---|
| | Left | Right | Left | Right |
| Accuracy (mm) | 1.73 ± 0.75 | 1.21 ± 0.63 | 1.61 ± 0.72 | 1.15 ± 0.62 |

Example 3—MR-Based Tracking Test

The robot was mounted on a skull model and placed and scanned inside a head coil. To reveal the brain phantom in the MR image, a "brain" was fabricated from agar gel in order to enhance the image contrast for needle targeting. Two thin tracking coil films were first employed and embedded in the needle guide. 3D spoiled gradient recalled-echo (SPGR) sequence was used to assess the location and orientation of the needle guide. The sequence parameters are stated in Table 2.

TABLE 2

MRI scan parameters

| | w/o needle inserted | w/needle inserted | SNR test |
|---|---|---|---|
| FOV(mm) | 240 × 240 | 240 × 240 | 280 × 280 |
| Matrix | 256 × 256 | 256 × 256 | 256 × 256 |
| Acquisition | FSPGR | FSPGR | T2-FSE |
| TR(ms) | 68.0 | 68.0 | 2000.0 |
| TE(ms) | 2.8 | 2.8 | 76.8 |
| Flip angle (°) | 10 | 10 | 90 |

A phantom needle made of carbon fiber was then inserted and scanned with the same imaging sequence. FIG. 8b showed the signal intensities of the two coils were 1133.00 and 1341.00, in contrast to the two circular areas comprising 59 pixels, which were sample on the background and agar gel brain, respectively, with average signal intensities of 116.26 and 232.05. FIG. 8c shows the resultant MR image in coronal view.

Example 4—MRI-Compatibility Test

Figure 11:
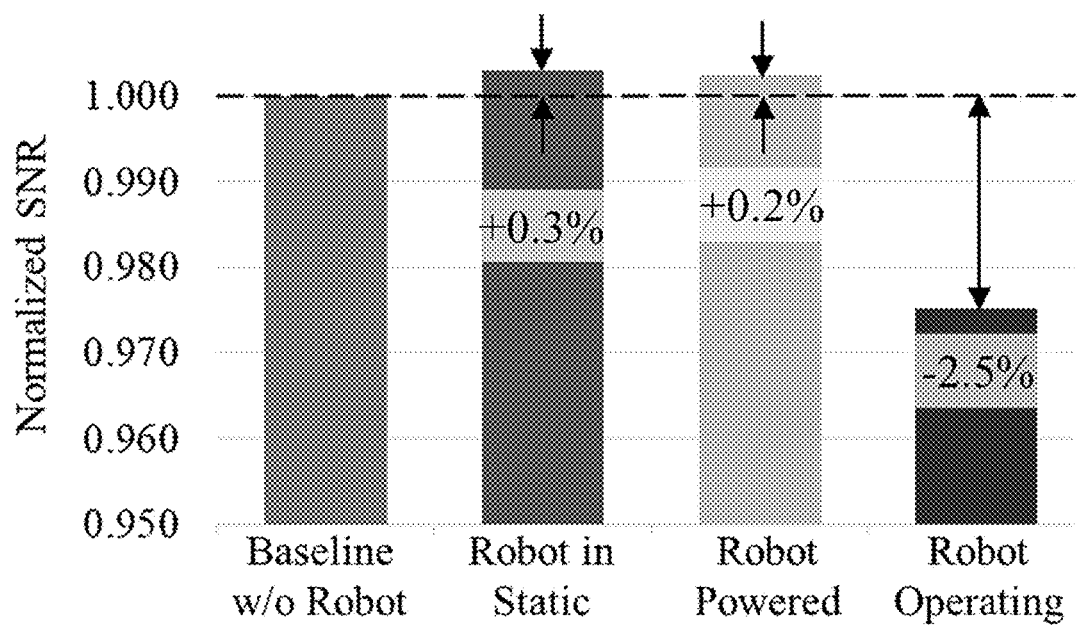
FIG. 11 is a plot of signal-to-noise ratio (SNR) test results.

The MRI-compatibility test was conducted in a 1.5 T MRI scanner (see, for example, FIG. 9). A square SNR phantom was placed at the isocenter of the scanner. A control image without the presence of the robot was acquired using a T2-weighted fastspin echo (FSE) sequence. Upon introducing the robot, MR images were obtained under three different robot operating conditions (see, for example, FIGS. 10 and 11). The operating conditions were i) static: the robot was introduced and remained powered off, ii) powered: the robot remains still, but the hydraulic and electrical power is on, and iii) operation: the robot is in full operation. The SNR ration was calculated as follows:

$$SNR = \frac{P_{center}}{SD_{center}} \quad (7)$$

Where $P_{center}$ is the mean value of the pixels region at the image center, $SD_{center}$ is the standard deviation of the pixels region at the lower right corner. The SNR loss is within 3% even with the robot in full motion and no observable image artifacts were generated.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A surgical robot for magnetic resonance imaging guided interventions, comprising:
   a manipulator comprising a tendon-based upper actuator and a tendon-based lower actuator;
   a mounting base connected to the lower actuator;
   a needle guide; and
   a needle disposed within the needle guide;
   wherein each of the tendon-based upper actuator and the tendon-based lower actuator comprises:
      a housing with a plurality of openings each configured to allow a tendon to pass therethrough;
      two rotational joints connected to the housing;
      two upper arms connected to the two rotational joints, respectively;
      two forearms connected to the two upper arms, respectively, at a proximal end of each forearm by a passive joint; and
      a passive ball joint connecting the two forearms at the distal end of each forearm,
   wherein the needle guide is disposed within the ball joint of the upper actuator and of the lower actuator, and
   wherein the mounting base has a plurality of screw holes for bone mounting.

2. The surgical robot of claim 1, further comprising a needle stop and/or a linear actuator disposed on the needle.

3. The surgical robot of claim 1, further comprising one or more MR-based trackers disposed on the needle guide.

4. The surgical robot of claim 1, wherein the robot includes a plurality of manipulators.

5. The surgical robot of claim 1, wherein the surgical robot is configured to be mounted on a skull.

6. The surgical robot of claim 1, wherein the needle is a rigid straight surgical instrument.

7. The surgical robot of claim 1, further comprising:
   four tendons, the four tendons comprising two tendons inserted into the housing of the tendon-based upper actuator and two tendons inserted into the housing of the tendon-based lower actuator; and
   two or more spools connected to each tendon of the four tendons, respectively,
   wherein each tendon of the four tendons is connected to each rotational joint of each housing, respectively.

8. The surgical robot of claim 7, wherein each tendon of the four tendons is channeled through a sheath, respectively.

9. The surgical robot of claim 8, further comprising:
   a first set comprising a plurality of pinion gears and rack gears, wherein each pinion gear of the first set is coupled to each spool, respectively; and
   a plurality of hydraulic tubes, each tube connected at a first end to each rack gear of the first set, respectively, and filled with fluid,
   wherein the fluid and each rack gear of the first set are separated by a first rolling diaphragm.

10. The surgical robot of claim 9, further comprising:
    a second set comprising a plurality of pinion gears and rack gears,
    wherein each pinion gear of the second set is coupled to a motor,
    wherein each rack gear of the second set is connected to an opposite end of each hydraulic tube, respectively, and
    wherein the fluid and each rack gear of the second set are separated by a second rolling diaphragm.

11. A surgical robot for magnetic resonance imaging guided interventions, comprising:
    two manipulators, each manipulator comprising a tendon-based upper actuator and a tendon-based lower actuator;
    each tendon-based lower actuator of the two manipulators connected to a mounting base;
    two needle guides; and
    two needles, each needle disposed within a respective needle guide,
    wherein each tendon-based upper actuator of the two manipulators and each tendon-based lower actuator of the two manipulators comprises:
       a housing with a plurality of openings each configured to allow a tendon to pass therethrough;
       two rotational joints connected to the housing;
       two upper arms connected to the two rotational joints, respectively;
       two forearms connected to the two upper arms, respectively, at a proximal end of each forearm by a passive joint; and
       a passive ball joint connecting the two forearms at the distal end of each forearm,
    wherein one of the needle guides is disposed within the ball joint of both the tendon-based upper actuator and the tendon-based lower actuator of each manipulator, respectively, and
    wherein the mounting base has a plurality of screw holes for bone mounting.

12. The surgical robot of claim 11, further comprising two needle stops and/or two linear actuators, each needle stop/linear actuator disposed on a respective needle.

13. The surgical robot of claim 11, further comprising two or more MR-based trackers, each MR-based tracker disposed on a respective needle guide.

14. The surgical robot of claim 11, further comprising:
    a first set comprising a plurality of pinion gears and rack gears, wherein each pinion gear of the first set is coupled to each spool, respectively; and
    a plurality of hydraulic tubes, each tube connected at a first end to each rack gear of the first set, respectively, and filled with fluid,
    wherein the fluid and each rack gear of the first set are separated by a first rolling diaphragm.

15. The surgical robot of claim 11, further comprising:
a second set comprising a plurality of pinion gears and rack gears,
wherein each rack gear of the second set is connected to an opposite end of each hydraulic tube, respectively, and
wherein the fluid and each rack gear of the second set are separated by a second rolling diaphragm.

16. The surgical robot of claim 11, wherein the surgical robot is configured to be mounted on a skull.

17. The surgical robot of claim 11, wherein each needle of the two needles is a rigid straight surgical instrument.

18. The surgical robot of claim 11, further comprising:
eight tendons, the eight tendons comprising two tendons inserted into the housing of each tendon-based upper actuator of the two manipulators and two tendons inserted into the housing of each tendon-based lower actuator of the two manipulators; and
two or more spools connected to each tendon, respectively,
wherein each tendon of the eight tendons is connected to each rotational joint of each housing, respectively.

19. The surgical robot of claim 18, wherein each tendon of the eight tendons is channeled through a sheath, respectively.

* * * * *